US007270287B2

(12) United States Patent
First

(10) Patent No.: US 7,270,287 B2
(45) Date of Patent: Sep. 18, 2007

(54) BOTULINUM TOXIN TREATMENT FOR KINESIA

(75) Inventor: Eric R. First, Boston, MA (US)

(73) Assignee: Allergan, Inc., Irvine, CA (US)

(*) Notice: Subject to any disclaimer, the term of this patent is extended or adjusted under 35 U.S.C. 154(b) by 0 days.

(21) Appl. No.: 10/752,869

(22) Filed: Jan. 6, 2004

(65) Prior Publication Data

US 2005/0147625 A1 Jul. 7, 2005

(51) Int. Cl.
A61K 39/08 (2006.01)
(52) U.S. Cl. .................................. 242/239.1
(58) Field of Classification Search ............ 514/2;
424/247.1
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,674,205 A | 10/1997 | Pasricha et al. | |
| 5,714,468 A | 2/1998 | Binder | |
| 5,766,605 A | 6/1998 | Sanders et al. | |
| 5,989,545 A | 11/1999 | Foster et al. | |
| 6,063,768 A | 5/2000 | First | |
| 6,139,845 A | 10/2000 | Donovan | |
| 6,265,379 B1 | 7/2001 | Donovan | |
| 6,299,893 B1 | 10/2001 | Schwartz et al. | |
| 6,306,423 B1 | 10/2001 | Donovan et al. | |
| 6,312,708 B1 | 11/2001 | Donovan | |
| 6,358,926 B2 | 3/2002 | Donovan | |
| 6,423,319 B1 | 7/2002 | Brooks et al. | |
| 6,458,365 B1 | 10/2002 | Aoki et al. | |
| 6,464,986 B1 | 10/2002 | Aoki et al. | |

OTHER PUBLICATIONS

Wenzel R.G., Am J Health Syst Pharm. 2004, vol. 61(22 Suppl 6): S5-10, esp. S6: col. 3, paragraph 4 and S10: col. 2, paragraph 2.*
Ansved et al., Neurology May 1997, 48 (5):1440-2, Abstract only.*
Billante et al., Muscle & Nerve Sep. 2002 26(3):395-403.*
U.S. Appl. No. 10/194,805, filed Jul. 11, 2002, Donovan.
Anderson, T., et al., *Surgical intervention for sinusitis in adults*, Curr Allergy Asthma Rep May 2001;1(3):282-8.
Aoki, K., et al., *Botulinum toxin type A and other botulinum toxin serotypes: a comparative review of biochemical and pharmacological actions*, Eur J. Neurol 2001: (suppl 5); 21-29.
Aoki, K., *Physiology and pharmacology of therapeutic botulinum neurotoxins*, in Kreyden, O., editor, Hyperhydrosis and botulinum toxin in dermatology, Basel, Karger; 2002; 30: pp. 107-116, at 109-110.
Barrientos, N., et al., *Efficacy and safety of butulinum toxin type A (Botox) in the prophylactic treatment of migraine*, Headache May 2002;42(5):452.
Bigalke H., et al., *Botulinum A Neurotoxin Inhibits Non-Cholinergic Synaptic Transmission in Mouse Spinal Cord Neurons in Culture*, Brain Research 360;318-324:1985.

Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981.
Binz T. et al., *The Complete Sequence of Botulinum Neurotoxin Type A and Comparision with Other Clostridial Neurotoxins*, J Biological Chemistry 265(16);9153-9158:1990.
Brem, H., et al, *Placebo-Controlled Trial of Safety and Efficacy of Intraoperative Controlled Delivery by Biodegradable Polymers of Chemotherapy for Recurrent Gliomas*Lancet 345:1008-1012:1995.
Brin, M., et al., *Botulinum toxin type A: pharmacology*, in Mayer N., editor, Spasticity: etiology, evaluation, management and role of botulinum toxin, 2002; pp. 110-124, at 112-113.
Bushara K., *Botulinum toxin and rhinorrhea*, Otolaryngol Head Neck Surg 1996;114(3):507.
Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (supp 2): R17.
Duggan et al.; *A survey of Botulinum neurotoxin substrate expression in cells; Mov Disord*, 10(3):376:1995.
Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.
Gonelle-Gisprt et al.; *Snap -25a and -25b isoforms are both expressed in insulin-secreting cells and can function in insulin secretion*; Biochem J 1;339 (pt 1):159-65:1999.
Guyton A.C. et al., *Textbook of Medical Physiology*, W.B. Saunders Company 1996, ninth edition pp. 686-688.
Habermann E., et al., *Tetanus Toxin and Botulinum A and C Neurotoxins Inhibit Noradrenaline Release From Cultured Mouse Brain*, J Neurochem 51(2);522-527:1988).
Habermann E., *Inhibition by Tetanus and Botulinum A Toxin of the release of [3H]Noradrenaline and [3H]GABA From Rat Brain Homogenate*, Experientia 44;224-226:1988.
Habermann, E.; I-Labeled Neurotoxin from Clostridium Botulinum A: Preparation Binding to Synaptosomes and Ascent to the Spinal Cord; Nauny-Schmiedeberg's Arch. Pharmacol, 1974; 281, 47-56.
*Harrison's Principles of Internal Medicine* (1998), edited by Anthony Fauci et al., 14th edition, published by McGraw Hill.
Jankovic J. et al., *Therapy With Botulinum Toxin*, Marcel Dekker, Inc., (1994), p. 5, 150.
Kohl R., et al., *Motion sickness: a modulatory role of the central cholinergic nervous system*Neuroscience and Biobehavioral Review 7:73-75, 1983.
Kreyden O, *Botulinum toxin: From poison to pharmaceutical: The history of a poison that became useful to mankind*, Kreyden OP, editor. Hyperhidrosis and Botulinum Toxin in Dermatology. Current Problems in Dermatology: Basel, Karger;2002;30:pp. 94-100.

(Continued)

Primary Examiner—Gary B. Nickol
Assistant Examiner—Cherie Woodward
(74) Attorney, Agent, or Firm—Claude L. Nassif; Stephen Donovan; Martin A. Voet

(57) ABSTRACT

Methods for treating kinesia (motion sickness) by local administration of a Clostridial toxin, such as a *botulinum* toxin, to a cranial or neck area of a patient susceptible to motion sickness.

14 Claims, No Drawings

OTHER PUBLICATIONS

Mast J., et al., *Successful pain management for Botox injections: A holistic approach*, Ann Neurol 2002;52(3):S157.

Miller T., et al., *Botulinum toxin A (Allergan) for chronic intractable headache Equally effective with or without concomitant neck pain*, Headache Jun. 2003;43(5):579.

Mittelstaedt H., *Somatic graviception*, Biol Psychol 42:53-74, 1996.

Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.

Naumann et al.; *Botulinum toxin type A in the treatment of focal, axillary and palmar hyperhidrosis and other hyperhidrotic conditions*; European J. Neurology 6 (Supp 4): S111-S1150:1999.

Oman C., *Motion sickness: a synthesis and evaluation of the sensory conflict theory*, Can J Physiol Pharmacol 68:294-303, 1990.

Pearce, L.B., *Pharmacologic Characterization of Botulinum Toxin For Basic Science and Medicine*, Toxicon 35(9);1373-1412 at 1393.

Ragona et al.; *Management of Parotid Sialocele With Botulinum Toxin; The Laryngoscope* 109:1344-1346:1999.

Robb N., *The risks of Botox*, Harv Womens Health Watch Nov. 2002;10(3):8.

Sanchez-Prieto, J., et al., *Botulinum Toxin A Blocks Glutamate Exocytosis From Guinea Pig Cerebral Cortical Synaptosomes*, Eur J. Biochem 165;675-681:1897.

Schantz, E.J., et al, *Properties and use of Botulinum toxin and Other Microbial Neurotoxins in Medicine*, Microbiol Rev. 56;80-99:1992.

Singh, *Critical Aspects of Bacterial Protein Toxins*, pp. 63-84 (chapter 4) of Natural Toxins II, edited by B.R. Singh et al., Plenum Press, New York (1976).

Sloop et al.; *Reconstituted Botulinum toxin type A does not lose potency in humans if it is refrozen or refrigerated for 2 weeks before use*; Neurology, 48:249-53:1997.

Wiegand et al. I-Labelled Botulinum A Neurotoxin: Pharmacokinetics inCats after Intramuscular Injection; *Nauny-Schmiedeberg's Arch. Pharmacol.* 1976; 292, 161-165.

* cited by examiner

BOTULINUM TOXIN TREATMENT FOR KINESIA

BACKGROUND

The present invention relates to methods for treating kinesia. In particular the present invention relates to methods for treating kinesia by local administration of a Clostridial neurotoxin to a human patient.

Motion Sickness

Upon experiencing motion, that is when traveling by car, boat, plane, while on an amusement park ride, etc, a person can suffer from kinesia. Kinesia is synonymous with motion sickness. The major or primary symptom of motion sickness is nausea. Most individuals have suffered or are susceptible to motion sickness. Typically, the rougher, more jarring or more prolonged a period of travel is the greater becomes the likelihood that a person will suffer form motion sickness, to varying degrees. Children, headache suffers, and woman (especially during menstruation and pregnancy) are particularly likely to experience motion sickness. Thus motion sickness is widespread and millions have and continue to be afflicted by it.

The etiology of motion sickness is not clear. The sensory conflict theory indicates that motion sickness can occur when the brain interprets sensory messages regarding movement as inharmonious or in conflict with each other. Such sensory messages can be delivered to the brain by parts of the body that detect motion, including the vestibular receptors of the ears, the eyes, as well as by proprioceptors in the skin, muscles, and other tissues. When these incoming signals from sensory sites conflict with the brain's "positional memory" motion sickness can result. Additionally, motion sickness may be due to stimulation of the semicircular canals of the ears during travel or motion, such as while on a boat, plane, car, swing or rotating amusement park ride. The sensory conflict theory does not explain motion sickness produced by all conditions. Oman C., *Motion sickness: a synthesis and evaluation of the sensory conflict theory*, Can J Physiol Pharmacol 68:294-303, 1990. For example, visceral graviceptors may contribute to how the body determines its position and when a misalignment is sensed motion sickness may result. Mittelstaedt H., *Somatic graviception*, Biol Psychol 42:53-74, 1996.

Nausea

A significant symptom of motion sickness is nausea. Nausea can be defined as a sensation of wanting to be sick, that is to vomit. Vomiting is the act of expelling the contents of the stomach. Besides motion sickness, nausea and/or vomiting can also be associated with concussion or other brain injury, an infection (including a brain infection such as encephalitis or meningitis), intestinal blockage, appendicitis, migraine, tumor, and chemotherapy.

It is believed that nausea leads to vomiting when sufficient nausea engendering signals have been received by what is called a vomiting centre, located in the brainstem. The vomiting centre receives information which can engender a sensation of nausea from four areas of the body; the chemoreceptor trigger zone; the vestibular center; the brain cortex, and from the gut (gastrointestinal tract). The chemoreceptor trigger zone comprises neurons in the brainstem which can sense changes in the chemical composition of the blood. Thus, many systemic analgesics (i.e. morphine, oxycodone, codeine, tramadol, methadone, hydromorphone) by affecting blood composition send signals to the chemoreceptor trigger zone which result in nausea.

The inner ear comprises the osseous labyrinth and the contained membranous labyrinth. The osseous labyrinth has three regions, the vestibule, the semicircular canals and the cochlea. The membranous labyrinth can be divided into the vestibular apparatus and the cochlear duct. In the walls of the membranous labyrinth within the vestibular apparatus are five distinct area of specialized sensory epithelium to which the terminal fibers of the vestibular nerve are distributed. The vestibular nuclei of the vestibular center located in the brainstem, receives and interprets information from the balance apparatus of the inner ear and compares it with the information received from the eyes. When the information received from the eyes is incongruent with the information received by the brain from the balance center, nausea can result. This is the mechanism of nausea through motion sickness.

The cortex is responsible for memory of unpleasant stimuli which have previously caused vomiting and this is called anticipatory nausea. Another example of cortex caused nausea is the nausea that can occur when a person sees blood or gore. Finally, nausea can also arise in the gut. Thus, sensors in the stomach and bowel can detect inflammation or irritation and upon transmission of this information to the chemoreceptor trigger zone produce nausea. Such gut induced nausea can be due for example to an ulcer in the stomach or duodenum, gastric reflux, severe constipation, food poisoning, infection, bowel obstruction, or presence of a tumor.

Drugs known to be effective against motion sickness include central cholinergic blockers and enhancers of dopamine-norepinephrine activity. These drugs act on various sites, including the vestibular receptors, the cerebellum, the reticular area, and the vomiting center Cholinergic blocker motion sickness drugs include scopolamine, atropine, dimenhydrinate, cyclizine, meclizine, and promethazine. Scopolamine is a belladonna alkaloid that acts like atropine. Like the other anticholinergics, it acts on muscarinic receptors. Scopolamine is effective to treat most types of motion. Unfortunately, common side effects of both oral and topical scopolamine are dry mouth and drowsiness.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex) 1 is a LD50 in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than *diphtheria*, about 600 million times more lethal than sodium cyanide, about 30 million times more lethal than cobra toxin and about 12 million times more lethal than *cholera*. Singh, *Critical Aspects of Bacterial Protein Toxins*, pages 63-84 (chapter 4) of Natural Toxins II, edited by B. R. Singh et al., Plenum Press, New York (1976) (where the stated LD50 of *botulinum* toxin type A of 0.3 ng equals 1 U is corrected for the fact that about 0.05 ng of BOTOX® equals 1 unit). One unit (U) of *botulinum* toxin is defined as the LD50 upon intraperitoneal injection into female Swiss Webster mice weighing 18 to 20 grams each.

Seven generally immunologically distinct *botulinum* neurotoxins have been characterized, these being respectively *botulinum* neurotoxin serotypes A, B, C1, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate LD50 for *botulinum* toxin type A. Moyer E et al., *Botulinum Toxin Type B: Experimental and Clinical Experience*, being chapter 6, pages 71-85 of "Therapy With *Botulinum* Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of *botulinum* toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light chain, L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype C1 was originally thought to cleave syntaxin, but was found to cleave syntaxin and SNAP-25. Each of the botulinum toxins specifically cleaves a different bond, except *botulinum* toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a *botulinum* toxin type A complex has been approved by the U.S. Food and Drug Administration for the treatment of blepharospasm, strabismus and hemifacial spasm. Subsequently, a *botulinum* toxin type A was also approved by the FDA for the treatment of cervical dystonia and for the treatment of glabellar lines, and a *botulinum* toxin type B was approved for the treatment of cervical dystonia. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months, although significantly longer periods of therapeutic activity have been reported.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type C1 has been shown to cleave both syntaxin and SNAP-25. These differences in mechanism of action may affect the relative potency and/or duration of action of the various *botulinum* toxin serotypes. Apparently, a substrate for a *botulinum* toxin can be found in a variety of different cell types. See e.g. *Biochem J* 1;339 (pt 1):159-65:1999, and *Mov Disord*, 10(3):376: 1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by Clostridial *bacterium* as complexes comprising the 150 kD *botulinum* toxin protein molecule along with associated non-toxin proteins. Thus, the *botulinum* toxin type A complex can be produced by Clostridial *bacterium* as 900 kD, 500 kD and 300 kD forms. *Botulinum* toxin types B and C1 is apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2);522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165;675-681:1897. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9);1373-1412 at 1393; Bigalke H., et al., *Botulinum A Neurotoxin Inhibits Non-Cholinergic Synaptic Transmission in Mouse Spinal Cord Neurons in Culture*, Brain Research 360;318-324:1985; Habermann E., *Inhibition by Tetanus and Botulinum A Toxin of the release of [3H]Noradrenaline and [3H]GABA From Rat Brain Homogenate*, Experientia 44;224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316;244-251:1981, and; Jankovic J. et al., *Therapy With Botulinum Toxin*, Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geq 3\times 10^7$ U/mg, an A260/A278 of less than 0.60 and a distinct pattern of banding on gel electrophoresis. The known Shantz process can be used to obtain crystalline *botulinum* toxin type A, as set forth in Shantz, E. J., et al, *Properties and use of Botulinum toxin and Other Microbial Neurotoxins in Medicine*, Microbiol Rev. 56;80-99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of 1-2×10⁸ LD50 U/mg or greater; purified *botulinum* toxin type B with an approximately 156 kD molecular weight with a specific potency of 1-2×10⁸ LD50 U/mg or greater, and; purified *botulinum* toxin type F with an approximately 155 kD molecular weight with a specific potency of 1-2×10⁷ LD50 U/mg or greater.

*Botulinum* toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure *botulinum* toxin can also be used to prepare a pharmaceutical composition.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that *botulinum* toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that *botulinum* toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of *botulinum* toxin type A to treat a variety of clinical conditions has led to interest in other *botulinum* toxin serotypes. Two commercially available *botulinum* type A preparations for use in humans are BOTOX® available from Allergan, Inc., of Irvine, Calif., and DYSPORT® available from Beaufour Ipsen, Porton Down, England. A *Blotulinum* toxin type B preparation (MYOBLOC®) is available from Elan Pharmaceuticals of San Francisco, Calif.

In addition to having pharmacologic actions at the peripheral location, *botulinum* toxins may also have inhibitory effects in the central nervous system. Work by Weigand et al, *Nauny-Schmiedeberg's Arch. Pharmacol*. 1976; 292, 161-165, and Habermann, *Nauny-Schmiedeberg's Arch. Pharmacol*. 1974; 281, 47-56 showed that *botulinum* toxin is able to ascend to the spinal area by retrograde transport. As such, a *botulinum* toxin injected at a peripheral location, for example intramuscularly, may be retrograde transported to the spinal cord.

U.S. Pat. No. 5,989,545 discloses that a modified clostridial neurotoxin or fragment thereof, preferably a *botulinum* toxin, chemically conjugated or recombinantly fused to a particular targeting moiety can be used to treat pain by administration of the agent to the spinal cord.

A *botulinum* toxin has also been proposed for the treatment of otitis media of the ear (U.S. Pat. No. 5,766,605), inner ear disorders (U.S. Pat. Nos. 6,265,379; 6,358,926), tension headache, (U.S. Pat. No. 6,458,365), migraine headache (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal *botulinum* toxin administration (U.S. patent application Ser. No. 10/194805).

A clinical symptom of botulism (*botulinum* toxin intoxication) is nausea and vomiting. Kreyden O, *Botulinum toxin: From poison to pharmaceutical: The history of a poison that became useful to mankind*, in: Kreyden O P, editor. *Hyperhidrosis and Botulinum Toxin in Dermatology. Current Problems in Dermatology*: Basel, Karger; 2002;30:pp. 94-100. Typically when a patient is administered a therapeutic dose of *botulinum* toxin to treat a migraine headache, the patient also experiences less of the nausea that is associated with the migraine headache. Barrientos, N., et al., *Efficacy and safety of botulinum toxin type A (Botox) in the prophylactic treatment of migraine*, Headache 2002 May; 42(5):452. Notably, the nausea associated with migraine is a secondary effect of the primary pain of migraine. Thus, a reduction of a migraine headache pain with a *botulinum* toxin only indirectly affects the nausea associated with migraine, and then only concomitantly with and following upon a reduction of the migraine pain.

Additionally, it is believed that the nausea of migraine may be generated in the upper brain, specifically in the upper cortex, while the motion sickness attendant to nausea may be generated in a lower brain area, such as in or near the fourth ventricle and/or medulla.

Significantly though it is has been reported that administration of a *botulinum* toxin into a head or neck muscle to treat headache can result in nausea or vomiting. Miller T., et al., *Botulinum toxin A (Allergan) for chronic intractable headache: Equally effective with or without concomitant neck pain*, Headache 2003 June;43(5):579. Additionally, it is has been reported that administration of a *botulinum* toxin into a muscle spasticity and pain can result in the patient experiencing nausea and/or vomiting. Mast J., et al., *Successful pain management for Botox injections: A holistic approach*, Ann Neurol 2002;52(3):S157. Further, it is known that administration of a *botulinum* toxin to a facial muscle to treat frowns and wrinkles can result in nausea. Robb N., *The risks of Botox*, Harv Womens Health Watch 2002 November;10(3):8.

Importantly, it is known that cholinergic innervation can play a role in motion sickness. Kohl R., et al., *Motion sickness: a modulatory role or the central cholinergic nervous system*, Neuroscience and Biobehavioral Review 7:73-75, 1983.

Tetanus toxin, as wells as derivatives (i.e. with a non-native targeting moiety), fragments, hybrids and chimeras thereof can also have therapeutic utility. The tetanus toxin bears many similarities to the *botulinum* toxins. Thus, both the tetanus toxin and the *botulinum* toxins are polypeptides made by closely related species of *Clostridium* (*Clostridium tetani* and *Clostridium botulinum*, respectively). Additionally, both the tetanus toxin and the *botulinum* toxins are dichain proteins composed of a light chain (molecular weight about 50 kD) covalently bound by a single disulfide bond to a heavy chain (molecular weight about 100 kD). Hence, the molecular weight of tetanus toxin and of each of the seven *botulinum* toxins (non-complexed) is about 150 kD. Furthermore, for both the tetanus toxin and the *botulinum* toxins, the light chain bears the domain which exhibits intracellular biological (protease) activity, while the heavy chain comprises the receptor binding (immunogenic) and cell membrane translocational domains.

Further, both the tetanus toxin and the *botulinum* toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of *botulinum* toxin by peripheral cholinergic neurons results in little if any retrograde transport, inhibition of acetylcholine exocytosis from the intoxicated peripheral motor neurons and a flaccid paralysis.

Finally, the tetanus toxin and the *botulinum* toxins resemble each other in both biosynthesis and molecular architecture. Thus, there is an overall 34% identity between the protein sequences of tetanus toxin and *botulinum* toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a therapeutically effective method for treating motion sickness, nausea and/or vomiting.

SUMMARY

The present invention meets this need and provides methods for effectively treating motion sickness, nausea and/or vomiting by local administration of a Clostridial toxin.

A method within the scope of the present invention for treating motion sickness can have the step of local administration of a Clostridial toxin to a head or neck of a patient, such as to a forehead, temple, brow or ear of a patient. Preferably, the Clostridial neurotoxin is administered to an individual who is susceptible to motion sickness from one hour to up to two weeks prior to engagement by the individual in an activity (i.e. travel) which can subject him to motion sickness. By local administration it is meant that the Clostridial toxin is administered, as by injection, directly to, in, or to the vicinity of, a region of the head or neck. Additionally, the Clostridial neurotoxin can be administered by injection into the middle or inner ear to treat motion sickness sensations which originate in the balance center of the ear.

The neurotoxin can be locally administered in an amount of between about $10^{-3}$ units/kg of patient weight and about 35 U/kg of patient weight. Preferably, the neurotoxin is locally administered in an amount of between about $10^{-2}$ U/kg and about 25 U/kg of patient weight. More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 10 U of a neurotoxin, such as *botulinum* toxin type A, into an inner ear structure or by topical application or by subdermal administration, to effectively treat (prophylacticly) motion sickness.

A suitable neurotoxin for use in the practice of the present invention can be made by a Clostridial *bacterium*, such as *Clostridium botulinum, Clostridium butyricum* or *Clostridium beratti*. The neurotoxin use can be a modified neurotoxin, that is a neurotoxin has had at least one of its amino acids deleted, modified or replaced, as compared to a native neurotoxin. Additionally, the neurotoxin can be recombinantly made produced neurotoxin or a derivative or fragment of a recombinant made neurotoxin. The neurotoxin can be a *botulinum* toxin, such as one of the *botulinum* toxin serotypes A, B, $C_1$, D, E, F or G. A preferred *botulinum* toxin to use in the practice of the present invention is *botulinum* toxin type A.

A method according to my invention can be carried out by administration of a Clostridial toxin to a patient with, or who is predisposed to, motion sickness. The Clostridial toxin used is preferably a *botulinum* toxin (as either a complex or as a pure [i.e. about 150 kDa molecule], such as a *botulinum* toxin A, B, C, D, E, F or G. Administration of the Clostridial toxin can be by a transdermal route (i.e. by application of a Clostridial toxin in a cream, patch or lotion vehicle), subdermal route (i.e. subcutaneous or intramuscular) or intradermal route of administration.

A hypothesized physiological reason for the efficacy of my invention, as explained in greater detail below, is to reduce, inhibit or eliminate sensory input (afferent) from the periphery into the central nervous system (including to the brain) which sensory input can result in a sensation of nausea. Such nausea inducing sensory input can be attenuated or eliminated by targeting subdermal sensory neurons with a low dose of a Clostridial toxin.

The dose of a Clostridial toxin used according to the present invention is less than the amount of toxin that would be used to paralyze a muscle, since the intent of a method according to the present invention is not to paralyze a muscle but to reduce a sensory output from sensory neurons located in a head or neck area.

The following definitions apply herein:

"About" means approximately or nearly and in the context of a numerical value or range set forth herein means ±10% of the numerical value or range recited or claimed.

"Alleviating" means a reduction in the occurrence of a motion sickness symptom. Thus, alleviating includes some reduction, significant reduction, near total reduction, and total reduction of a motion sickness symptom. An alleviating effect may not appear clinically for between 1 to 7 days after administration of a Clostridial toxin to a patient.

"*Botulinum* toxin" means a *botulinum* neurotoxin as either pure toxin (i.e. about 150 kDa weight molecule) or complex (i.e. 300-900 kDa weight complex), and excludes *botulinum* toxins which are not neurotoxins such as the cytotoxic *botulinum* toxins C2 and C3, but includes recombinantly made, hybrid, modified, and chimeric *botulinum* toxins.

"Local administration" or "locally administering" means administration (i.e. by a subcutaneous, intramuscular, subdermal or transdermal route) of a pharmaceutical agent to or to the vicinity of a subdermal location or in the head or neck of a patient.

"Treating" means to alleviate (or to eliminate) at least one symptom of a motion sickness, either temporarily or permanently.

The Clostridial neurotoxin is administered in a therapeutically effective amount to alleviate a symptom of a motion sickness. A suitable Clostridial neurotoxin may be a neurotoxin made by a *bacterium*, for example, the neurotoxin may be made from a *Clostridium botulinum, Clostridium butyricum*, or *Clostridium beratti*. In certain embodiments of the invention, the motion sickness can be treated by intramuscular (facial) administration a *botulinum* toxin to the patient. The *botulinum* toxin may be a *botulinum* toxin type A, type B, type C1, type D, type E, type F, or type G. The nausea alleviating effects of the *botulinum* toxin may persist for between about 2 weeks (i.e. upon administration of a short acting *botulinum* toxin, such as a *botulinum* toxin type E) and 5 years (i.e. upon implantation of a controlled release *botulinum* toxin implant). The *botulinum* neurotoxin can be a recombinantly made *botulinum* neurotoxins, such as *botulinum* toxins produced by an *E. coli* bacterium. In addition or alternatively, the *botulinum* neurotoxin can be a modified neurotoxin, that is a *botulinum* neurotoxin which has at least one of its amino acids deleted, modified or replaced, as compared to a native or the modified *botulinum* neurotoxin can be a recombinant produced *botulinum* neurotoxin or a derivative or fragment thereof.

A method for treating a motion sickness according to the present invention can comprise the step of local administration of a *botulinum* toxin to a patient predisposed to experience a motion sickness to thereby alleviate the motion sickness. The *botulinum* toxin can be selected from the group consisting of *botulinum* toxin types A, B, C, D, E, F and G. *Botulinum* toxin type A is a preferred *botulinum* toxin.

A detailed embodiment of my invention can comprise a method for treating a motion sickness by local administration to a patient with a motion sickness of between about 1 unit and about 3,000 units of a *botulinum* toxin (for example between about 1-50 units of a *botulinum* toxin type A or between about 50 to 3,000 units of a *botulinum* toxin type B), thereby alleviating the motion sickness for between about two weeks and about 5 years.

My invention also encompasses a method for treating motion sickness by locally administering a *botulinum* toxin (such as a *botulinum* toxin type A, B, C, D, E, F or G, in an amount of from 1 unit to 3,000 units per treatment session) to a patient predisposed to experience motion sickness, thereby preventing the patient from experiencing motion sickness. A patient predisposed to motion sickness is a human who has experienced motion sickness at least once within the last twelve months while traveling by boat, car, or airplane or while on an amusement park ride. The local administration can be carried out by intramuscular, subcutaneous or by topical administration of the *botulinum* toxin a location on or within a head or neck of the patient, such as to a forehead of the patient or to a facial muscle, such as to a frontalis muscle of the patient. The *botulinum* toxin can be administered to a subdermal head or neck location of a patient.

In another embodiment of my invention, motion sickness can be treated by first selecting a patient who has experienced motion sickness upon engaging in a first motion sickness engendering activity. A patient can be "selected" by a decision by a physician to treat a patient. A first motion sickness engendering activity can be an activity such as travel by boat, car, or airplane or being on an amusement park ride. The next step in this method can be administering a *botulinum* toxin to the selected patient. The third step in this method for treating motion sickness can be observing a reduced incidence of motion sickness in the patient when the patient engages in a second motion sickness engendering activity, thereby treating the motion sickness. The "observing" activity can be receipt by the treating physician of information (i.e. from the patient) regarding motion sickness, or a lack thereof, experienced by the patient at any time after the administration of the *botulinum* toxin to the patient. A "reduced incidence" means with a lesser occurrence of a motion sickness, or occurrence of a motion sickness with less severe or less unpleasant symptoms (i.e. with no or less nausea). A second motion sickness engendering activity can be the same as the first motion sickness engendering activity Administering the *botulinum* toxin can be carried out by local administration of a *botulinum* toxin to an ear, of the patient the ear comprising an outer ear, a middle ear and an inner ear. Thus, nausea associated with motion sickness can be treated by local administration of a therapeutic amount of a *botulinum* toxin to an ear of a human patient to thereby substantially alleviating nausea associated with motion sickness. Note that a symptom of motion sickness treated by the disclosed method can be pallor, nausea, weakness, malaise, vomiting, vertigo and dizziness.

A further embodiment of my invention is a method for treating nausea and/or vomiting associated with motion sickness by administering an effective amount of a *botulinum* toxin to thereby treating nausea and/or vomiting associated with motion sickness. The *botulinum* toxin can be administered in conjunction with an anitmemtic, such as dexamethasone, or ondansetron in combination with dexamethasone. The motion sickness can be a result of air travel, sea vessel travel or automobile travel.

My invention also encompasses a method for treating nausea and/or vomiting associated with a cancer chemotherapy (i.e. opiod therapy) or radiation therapy, by administering an effective amount of a *botulinum* toxin, thereby treating nausea and/or vomiting associated with a cancer chemotherapy. The *botulinum* toxin can be administered subcutaneously, intramuscularly or systemically (the later being a targeted toxin). Additionally, the *botulinum* toxin can be administered with a needle or by a needleless injection. The nausea can be reduced by from about 20% to 100%.

DESCRIPTION

The present invention is based upon the discovery that motion sickness can be treated by local administration of a therapeutically effective amount of a Clostridial toxin, such as a *botulinum* toxin. The *botulinum* toxin (such as a *botulinum* toxin serotype A, B, $C_1$, D, E, F or G) can be injected into or topically applied onto or in the vicinity of a head or neck region of a patient predisposed to motion sickness to thereby suppress a nausea and/or vomiting symptom of motion sickness. Alternately, the *botulinum* toxin can be administered to an intradermal or subdermal sensory neuron thereby suppressing and treating a symptom of a motion sickness.

Non-limiting examples of motion sickness and other conditions associated with nausea and vomiting are travel by in any type of moving vehicle, such as a boat, car or airplane. I have determined that pretreatment with *botulinum* toxin administered to i.e. the temporal muscles or in particular to an area innervated by the vestibular nerve can significantly reduce the incidence of nausea and vomiting associated with motion sickness. Cancer patients who suffer from a nausea and vomiting secondary to chemotherapy treatment can also be treated by the disclosed method.

I have surprisingly found that administration of a *botulinum* toxin to a patient predisposed to a motion sickness has a prophylactic and direct effect on the primary or major symptom of motion sickness, nausea.

A mechanism by which a *botulinum* toxin may inhibit or reduce nausea and vomiting is through its ability to inhibit release of neurotransmitters from sensory peripheral nerve branches involved in nausea and/or vomiting such as but not limited to acetylcholine, 5HT, glutamate and histamine. These nerve branches may arise from the cranial nerves V-VIII. Glutamate in particular appears to play a significant role in regulation of the vomiting center. Acetylcholine release, also thought to cause effects on the vomiting center could also be affected either directly or indirectly by a *botulinum* toxin.

What is surprising and unexpected with regard to my invention, is that direct application via subcutaneous administration of a therapeutically effective amount of a *botulinum* toxin can reduce or inhibit the nausea of motion sickness.

My invention is preferably practiced by administering a *botulinum* toxin directly to a head or neck area. An alternate preferred method for practicing the present invention is by pericranial administration of a *botulinum* toxin to a patient predisposed to a motion sickness, as by intramuscular injection of the *botulinum* toxin into the glabellar, frontalis and/or temporalis muscles of the patient.

Without wishing to be bound by theory a physiological mechanism can be proposed for the efficacy of the present invention. It is known that muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. As well as excitation by these two type of efferent anterior motor neuron projections, there are additional, afferent sensory neurons which project from muscle spindle and golgi tendon organs and act to transmit information regarding various muscle parameter status to the spinal cord, cerebellum and cerebral cortex. These afferent motor neurons which relay sensory information from the muscle spindle include type Ia and type II sensory afferent neurons. See e.g. pages 686-688 of Guyton A. C. et al., *Textbook of Medical Physiology*, W. B. Saunders Company 1996, ninth edition.

Significantly, it has been determined that a *botulinum* toxin can act to reduce transmission of sensory information from muscle type Ia afferent neurons. Aoki, K., *Physiology and pharmacology of therapeutic botulinum neurotoxins*, in Kreyden, O., editor, Hyperhydrosis and *botulinum* toxin in dermatology, Basel, Karger; 2002; 30: pages 107-116, at 109-110. And it has been hypothesized that *botulinum* toxin can have a direct effect upon muscle cell sensory afferents and modify signals from these afferents to the central nervous system. See e.g. Brin, M., et al., *Botulinum toxin type A: pharmacology*, in Mayer N., editor, Spasticity: etiology, evaluation, management and the role of *botulinum* toxin, 2002; pages 110-124, at 112-113; Cui, M., et al., *Mechanisms of the antinociceptive effect of subcutaneous BOTOX®: inhibition of peripheral and central nociceptive processing*, Naunyn Schmiedebergs Arch Pharmacol 2002; 365 (supp 2): R17; Aoki, K., et al., *Botulinum toxin type A and other botulinum toxin serotypes: a comparative review of biochemical and pharmacological actions*, Eur J. Neurol 2001: (suppl 5); 21-29. Thus, it has been demonstrated that *botulinum* toxin can cause an altered sensory output from muscle to CNS and brain.

Importantly, the sensory neurons from which afferent output is to be inhibited by a method according to the present invention need not be located on or within a muscle, but can be in an intradermal or subdermal location.

It can be postulated that a motion sickness can be due to a sensory input from afferent cranial or neck area neurons. Thus, administration of a *botulinum* toxin to a facial muscles or skin to reduce sensory output from the muscle can result in alleviation of a motion sickness symptom.

It is my hypothesis, as may be the case in the treatment of a migraine headache with a *botulinum* toxin, that signals transmitted by afferent nerves in or on muscle tissue (i.e. muscle spindle fibers and muscle pain fibers) or as a part of sensory structures in the skin or subdermally induce the nausea sensation of a motion sickness. That is, afferent signal from muscles or skin structures provide sensory information to the brain which then leads to the generation of nausea Thus, a local administration of a *botulinum* toxin to muscle spindle fibers or other sensors in or in the vicinity of a muscle can act to alter the neural signal afferent output from these muscles to the brain and thereby decrease the sensation of nausea associated with motion sickness.

The invention disclosed herein can be carried out by administering a *botulinum* neurotoxin intradermally, subcutaneously, topically (i.e. via transdermal patch) to regions innervated by the cranial nerves V-VIII, in particular, near the sensory branches of the auriculotempular branch of the trigeminal nerve, as this can influence the occurrence of motion sickness nausea. The *botulinum* neurotoxin can also be administered into the ear by the methodologies set forth supra. t A most preferred method for practicing the invention disclosed herein is to administer a *botulinum* neurotoxin around or near the ear, i.e. on the side of the head. Unlike treatment of migraine can be treated by administering a *botulinum* toxin on the front of the head, such as in the forehead, this most preferred method requires the *botulinum* toxin to be administered behind the ear and by the lobe of the ear, because this is where the cranial VIII (vestibular) nerve has easily accessible branches.

Important elements of my invention are firstly that is practised by use of a local administration of low dose of a *botulinum* toxin. The selected low dose does not cause a muscle paralysis. Secondly, the invention is practised by local administration of the low dose of the *botulinum* toxin to the muscle or to the muscle group which initiates the nausea sensation.

The amount of the Clostridial toxin administered according to a method within the scope of the disclosed invention can vary according to the particular characteristics of the motion sickness being treated, including its severity and other various patient variables including size, weight, age, and responsiveness to therapy. To guide the practitioner, typically, no less than about 1 unit and no more than about 50 units of a *botulinum* toxin type A (such as BOTOX®) is administered per injection site (i.e. to each muscle portion injected), per patent treatment session. For a *botulinum* toxin type A such as DYSPORT®, no less than about 2 units and no more about 200 units of the *botulinum* toxin type A are administered per injection site, per patent treatment session. For a *botulinum* toxin type B such as MYOBLOC®, no less than about 40 units and no more about 2500 units of the *botulinum* toxin type B are administered per injection site, per patent treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a *botulinum* toxin type A; for DYSPORT® no less than about 4 units and no more than about 100 units, and; for MYOBLOC®, no less than about 80 units and no more than about 1000 units are, respectively, administered per injection site, per patent treatment session.

Most preferably: for BOTOX® no less than about 5 units and no more than 15 units of a *botulinum* toxin type A; for DYSPORT® no less than about 20 units and no more than about 75 units, and; for MYOBLOC®, no less than about 200 units and no more than about 750 units are, respectively, administered per injection site, per patent treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity of a motion sickness perceived.

The present invention is based on the discovery that local administration of a Clostridial toxin can provide significant and long lasting relief from a motion sickness. The Clostridial toxins used in accordance with the invention disclosed herein can inhibit transmission of chemical or electrical signals between select neuronal groups that are involved in generation of a motion sickness symptom. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The motion sickness alleviation effect provided by the Clostridial toxin can persist for a relatively long period of time, for example, for more than two months, and potentially for several years.

Examples of Clostridial toxins within the scope of the present invention include neurotoxins made by *Clostridium botulinum, Clostridium butyricum* and *Clostridium beratti* species. In addition, the *botulinum* toxins used in the methods of the invention may be a *botulinum* toxin selected from a group of *botulinum* toxin types A, B, C, D, E, F, and G. In one embodiment of the invention, the *botulinum* neurotoxin administered to the patient is *botulinum* toxin type A. *Botulinum* toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

*Botulinum* toxins for use according to the present invention can be stored in lyophilized, vacuum dried form in containers under vacuum pressure or as stable liquids. Prior to lyophilization the *botulinum* toxin can be combined with pharmaceutically acceptable excipients, stabilizers and/or carriers, such as albumin. The lyophilized material can be reconstituted with saline or water to create a solution or composition containing the *botulinum* toxin to be administered to the patient.

Although the composition may only contain a single type of neurotoxin, such as *botulinum* toxin type A, as the active ingredient to suppress neurotransmission, other therapeutic compositions may include two or more types of neurotoxins, which may provide enhanced therapeutic treatment of a motion sickness. For example, a composition administered to a patient may include *botulinum* toxin type A and *botulinum* toxin type B. Administering a single composition containing two different neurotoxins may permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a motion sickness can include one or more neurotoxins, such as *botulinum* toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a *botulinum* toxin within a tissue appears to be a function of dose and can be graduated. Jankovic J., et al *Therapy With Botulinum Toxin*, Marcel Dekker, Inc., (1994), page 150. Thus, diffusion of *botulinum* toxin can be controlled to reduce potentially undesirable side effects that may affect the patient's cognitive abilities. For example, the neurotoxin can be administered so that the neurotoxin primarily effects neural systems believed to be involved in the generation of nausea inducing signals which result in motion sickness.

A polyanhydride polymer, GLIADEL® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation.

The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345;1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58;672-684:1998.

Local administration of a Clostridial toxin, such as a *botulinum* toxin, can provide a high, local therapeutic level of the toxin. A controlled release polymer capable of long term, local delivery of a Clostridial toxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a *botulinum* toxin, according to the present invention, by injection or implant to a target tissue provides a superior alternative to systemic administration of pharmaceuticals to patients to alleviate a motion sickness.

The amount of a Clostridial toxin selected for local administration to a target tissue according to the present disclosed invention can be varied based upon criteria such as the severity of the motion sickness being treated, the extent of muscle tissue to be treated, solubility characteristics of the neurotoxin toxin chosen as well as the age, sex, weight and health of the patient. For example, the extent of the area of muscle tissue influenced is believed to be proportional to the volume of neurotoxin injected, while the quantity of the suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by intramuscular injection, subcutaneous injection, by implantation of a controlled release implant or by topical application, as by use of a transdermal patch.

Example 1

Use of a *Botulinum* Toxin Type A to Treat Motion Sickness

A 40 year old male works in a field sales position and has a history of severe motion related sickness that at times limits his ability to travel. In this position, the patient primarily worked out of a home office but is required to go on sales trips quarterly. These trips can cause him a great deal of anxiety, which led to can lead to significant bouts of nausea and vomiting. The patient had tried numerous anti-emetics with no relief. The patient agrees to *botulinum* toxin type A injections 2 weeks prior to his next trip, which can be applied subcutaneously along the peripheral branches of the V-VII nerves in the temporal and frontal regions, in a dose of 2.5 units/2 $cm^2$ for a total of 35 units. The patient can report excellent relief, without nausea or vomiting.

Example 2

Use of a Transdermal *Botulinum* Toxin Type A to Motion Sickness

A 35 year old male who had a significant history of sea and air motion sickness was due to travel on a cruise ship for his honeymoon. The patient had tried numerous anti-emetics with no relief. The patient agrees to *botulinum* toxin anti-motion sickness patches prior to his cruise. Three weeks prior to his cruise two 1 $cm^2$ patches containing a slow release *botulinum* toxin formulation were applied along behind the ear: one in each region delivering a total of 25 units each via slow release. The patient reports excellent relief, with no associated nausea or vomiting.

Example 3

*Botulinum* Toxin Type A to Treat Nausea Related to Nerve Compression

A 27 year old female who has suffered from dizziness for 2 years and nausea for 1 year. The dizziness is caused by a compressed 8th cranial nerve and had recent surgery to correct it. However following surgery to correct these symptoms, adhesions were found all over this nerve which was caused by a virus, identified as herpes. Due to the adhesions, surgery is not an option and the patient agrees to a course of botulinum toxin. A *botulinum* toxin type A can be applied along the peripheral branches of the 8th nerve and intra-auricularily, in a dose of 2.5 U/2 cm² for a total of 25 Units. Surprisingly, the patient reports near complete relief 48 hours later, and can be free of any symptoms by day seven. The patient returns about every 6 months on average for repeat injections.

Example 4

*Botulinum* Toxin Type A to Treat Nausea Related to Chemotherapy

A 20-year-old female is diagnosed with a fibrolamellar hepatoma with extensive metastasis to nodes and organs. She is having "aggressive" chemotherapy with several negative side effects including intolerable nausea and vomiting, leading to discontinuation of treatment. *Botulinum* toxin type A is applied in the regions of cranial nerves V-VIII via intra dermal injection and intraauricularily, along the peripheral branches cranial nerves VIII, in a dose of 2.5 units/2 cm² for a total of 25 Units. The patient's symptoms of nausea and vomiting are dramatically reduced, and the patient reports significantly less discomfort and is able to return for further chemotherapy.

Example 5

*Botulinum* Toxin Type B to Treat Nausea Related to Radiotherapy

A 47 year old female cancer patient suffers from significant nausea and vomiting subsequent to cancer radiotherapy sessions. *Botulinum* toxin type B is applied in the regions of CN V-VIII via subcutaneous injection and intra-auricularily, along the peripheral branches cranial nerve, in a dose of 120 units/2 cm² for a total of 3750 Units. The patient's symptoms of both nausea and vomiting upon chemotherapy are dramatically reduced, and patient reports significantly less discomfort and was able to return to normal activity.

Example 6

*Botulinum* Toxin Type A Therapy for a Motion Sickness

A female patient, 32 years old, complains of frequent nausea while engaged in her amusement park ride maintenance job, which requires use of roller coaster, spinning top and other rides at the park. The patient is treated by injection of 10 units a *botulinum* toxin type A (i.e. BOTOX®) into each of the glabellar, frontalis and temporalis muscles (30 units total toxin). Within 1-7 days after the *botulinum* toxin administration the patient reports complete alleviation of her motion sickness which carrying out her job and alleviation of her condition can persist for 4-6 months.

A *botulinum* toxin type B, C, D, E, F or G can be substituted for the *botulinum* toxin type A used above, for example by use of 250 units of a *botulinum* toxin type B.

Example 7

Endoscopic Examination of the Middle Ear

It is known that one or two port endoscopy of the middle ear can be carried out. Thus, anatomical structures can be visualized by transmeatal or transtympanic rigid scopes of different angles and by a flexible scope in the eustachian tube. Three endoscopic routes to the middle ear can be used, these being: (1) transmeatal after raising a tympanomeatal flap, (2) transtympanic through a tympanic incision, and (3) the non-invasive through the preformed channel of the eustachian tube.

A transtympanic endoscope can be used to view the tympanic cavity. A flexible, steerable scope with an outside diameter of 0.8 mm (12,000 pixels; angle of view, 70°; total length, 650 mm; deflection angle, 90°; and length of deflectable part 25 mm) obtained from Micromed Co, Dornbirn, Austria can be used for transtubal endoscopy. The patient's head can be positioned in 30° lateral decubitus. The transtubal scope can be introduced through a tubal catheter placed at the pharyngeal orifice of the eustachian tube under endoscopic guidance (rigid 70° scope) through the contralateral nasal airway. After removing the rigid scope, the flexible steerable scope can be advanced into the middle ear through the tubal catheter. Successful advancement of the scope to the middle ear requires an adequate width of the tubal isthmus (mean, 1.0 mm wide and 2 mm high).

Transmeatal or transtympanic endoscopy can be performed using a rigid scope. Depending on the approach chosen, the outside diameter of the scope can be either 2.3 or 1.9 mm, with angles of 0°, 30°, or 70° (Karl Storz, Tuttlingen, and Aesculap). For the transmeatal approach, the tympanic cavity can be opened by endoscopically raising a tympanomeatal flap so that the scope can enter the posterior part of the cavity below the incudostapedial joint. For the transtympanic approach, radial incisions can be made in the tympanic membrane either between the posterosuperior and the posteroinferior quadrant or in the anteroinferior quadrant, depending on the region of interest. Images can be recorded on a digital image recording device from S-VHS video sources (Digi-Still Unit and S-VHS Video Recorder; Sony, Vienna, Austria).

The field of view available depends on the angle of the scope (0°, 30°, or 70°). The 0° scopes can provide visualization only of the long process of the incus and the medial wall (labyrinthine wall). The 30° scopes can afford a larger view in all directions. The field of view can extend to the facial canal with the scope directed upward, to the round window niche with the scope directed downward, to the tympanic sinus with the scope directed posteriorly, and to the cochleariform process with the scope directed anteriorly. The 70° scope can offer an even wider view of the tympanic cavity. With these, the tympanic chord and the aditus ad antrum can be seen above, the hypotympanum below, the lateral sinus and facial recess posteriorly, and the tympanic orifice of the tube anteriorly.

With a transtubal endoscope, the isthmus can be successfully negotiated and passage aided by subtly maneuvering and turning the scope tip. Once the steerable scope has reached the protympanum, it can be advanced along 2 alternative routes: (1) above the tensor tendon into the epitympanum and then along the tegmen to the mastoid antrum; or (2) below the tensor tendon into the mesotympanum toward the incudostapedial joint and then either (a) medial to the incus and above the stapes into the aditus ad antrum or (b) lateral to the incus toward the tympanic chord or (c) below the stapes toward the lateral sinus. As the scope is advanced through the mesotympanum, it passes the entire tympanic membrane, which forms the lateral wall and can be inspected in its entire extension. Along the routes described, the flexible scope can be easily maneuvered past the ossicles without injuring them.

In each of the following examples, the specific amount of BOTOX® administered depends upon a variety of factors to be weighed and considered within the discretion of the attending physician and in each of the examples insignificant amounts of *botulinum* toxin enter appear systemically with no significant side effects.

Example 8

Endoscopic Treatment of Motion Sickness

A 24 year old woman complains of motion sickness She experiences vertigo and nausea whenever she rides in a car. Transtympanic endoscopy is carried out, as set forth in Example 7, and from 1 unit to 50 units of a *botulinum* toxin A-G, such as BOTOX®, is injected directly into the patient's middle ear. Within 1-7 days the motion sickness is substantially alleviated and the symptoms do not return or return only after 2 to 4 months have elapsed after the single injection of the *botulinum* toxin.

Thus, the *botulinum* toxin can be administered by an endoscopic sinus procedure as set forth for example in Anderson, T., et al., *Surgical intervention for sinusitis in adults*, Curr Allergy Asthma Rep 2001 May;1(3):282-8 using the endoscopic injection instrument described in U.S. Pat. Nos. 5,437,291 and 5,674,205.

Example 9

Treatment of Motion Sickness

A 60 year old male complains bitterly of motion sickness whenever he rides an elevator. Transtympanic injection of a muscle relaxant (Xylocaine) is ineffective, as is masking, weight reduction and biofeedback. No venous turbulence or eustachian tube etiology or can be determined. From 1 unit to 50 units of a *botulinum* toxin A-G, such as BOTOX®, is injected into the vestibule in the vicinity of the cochleal nerve. Within 1-7 days the motion sickness is substantially alleviated and the symptoms do not return or return only after 2 to 6 months have elapsed after the *botulinum* toxin injection, once into or into the vicinity of the cocheal nerve.

Example 10

Treatment of Motion Sickness

A patient predisposed to experiencing motion sickness can be treated by administering from about 2.5 units to about 25 units of a *botulinum* toxin type A (i.e. BOTOX) intradermally, subcutaneously, topically (i.e. via transdermal patch) to regions innervated by the cranial nerves V-VIII, in particular, near the sensory branches of the auriculotempular branch of the trigeminal nerve. It is believed that this nerve branch can influence an occurrence of motion sickness nausea. The *botulinum* toxin can also be administered into the ear, as an intrauricular toxin administration.

Preferably the *botulinum* toxin is administered to the patient at a site on the lower side of the head, just behind an ear lobe, as at this location there are cranial VIII (vestibular) nerve with accessible branches. Another site of injection can be intra-auriculariy (in the ear) to target the cranial nerve VIII branches.

A method for treating motion sickness according to the invention disclosed herein has many benefits and advantages, including the following:

1. the symptoms of a motion sickness can be dramatically reduced or eliminated.

2. the symptoms of a motion sickness can be reduced or eliminated for at least about two weeks to about six months per injection of neurotoxin and for from about one year to about five years upon use of a controlled release neurotoxin implant.

3. the injected or implanted Clostridial neurotoxin shows little or no tendency to diffuse or to be transported away from the intramuscular (or intradermal or subdermal) injection or implantation site.

4. few or no significant undesirable side effects occur from intramuscular (or intradermal or subdermal) injection or implantation of the Clostridial neurotoxin.

5. the present methods can result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a motion sickness wherein two or more neurotoxins, such as two or more *botulinum* toxins, are administered concurrently or consecutively. For example, *botulinum* toxin type A can be administered until a loss of clinical response or neutralizing antibodies develop, followed by administration of *botulinum* toxin type B. Alternately, a combination of any two or more of the *botulinum* serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a *botulinum* toxin, begins to exert its therapeutic effect.

A *botulinum* toxin can be administered by itself or in combination of one or more of the other *botulinum* toxin serotypes. The *botulinum* toxin can be a recombinantly made or a hybrid *botulinum* toxin.

My invention also includes within its scope the use of a neurotoxin, such as a *botulinum* toxin, in the preparation of a medicament for the treatment of a motion sickness, by local administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method for treating motion sickness, the method comprising a step of administering subcutaneously, intramuscularly, subdermally or transdermally between about 1 unit and about 200 units of a *botulinum* toxin type A to a location of a frontalis muscle of the face a human patient predisposed to experience motion sickness, the administering step being carried out before the patient engages in a motion sickness engendering activity, thereby treating the motion sickness.

2. The method of claim 1, wherein the method treats a symptom of motion sickness selected from the group consisting of pallor, nausea, weakness, malaise, vomiting, vertigo and dizziness.

3. The method of claim 1 wherein the *botulinum* toxin is administered with a needle.

4. The method of claim 1 wherein the *botulinum* toxin is administered by needleless injection.

5. The method of claim 1 wherein the nausea is reduced by from about 20% to 100%.

6. A method for treating motion sickness, the method comprising the steps of:
   (a) selecting a patient who has experienced motion sickness upon engaging in a first motion sickness engendering activity, wherein said first motion engendering activity is selected from the group consisting of traveling by boat, car and airplane;
   (b) administering subcutaneously, intramuscularly, subdermally or transdermally, between about 1 unit and about 200 units of a *botulinum* toxin type A or type B into a glabellar, frontalis or temporalis muscle of the patient, and;
   (c) observing a reduced incidence of motion sickness in the patient when the patient engages in a second motion sickness engendering activity, wherein said second motion engendering activity is selected from the group consisting of traveling by boat, car and airplane, thereby treating motion sickness.

7. A method for treating nausea associated with motion sickness in a patient, the method comprising the step of administration subcutaneously, intramuscularly, subdermally or transdermally, between about 1 unit and about 200 units of a *botulinum* toxin type A or between about 40 to about 2500 units of *botulinum* toxin type B to an ear of a human patient who has experienced severe motion sickness and anxiety before engaging in a motion sickness engendering activity, thereby alleviating nausea associated with the severe motion sickness.

8. A method for treating nausea and/or vomiting associated with motion sickness, the method comprising the step of administering subcutaneously, intramuscularly, subdermally or transdermally, between about 1 unit and about 200 units of a *botulinum* toxin type A or between about 40 to about 2500 units of *botulinum* toxin type B to a glabellar, frontalis or temporalis muscle of a human patient who has experienced severe motion sickness and anxiety before engaging in a motion sickness engendering activity, thereby treating nausea and/or vomiting associated with motion sickness.

9. The method of claim 8 wherein the *botulinum* toxin is administered in conjunction with an anti-emetic.

10. The method of claim 8 wherein the motion sickness is a result of air travel.

11. The method of claim 8 wherein the motion sickness is a result of sea vessel travel.

12. The method of claim 8 wherein the motion sickness is a result of automobile travel.

13. A method for prophylactically treating motion sickness in a human patient before engaging in a motion sickness engendering activity, comprising the step of administering between about 1 unit and about 200 units of a *botulinum* toxin type A or between about 40 to about 2500 units of a *botulinum* toxin type B subcutaneously, intramuscularly, subdermally or transdermally behind an ear and by a lobe of said ear of said human patient, wherein said *botulinum* toxin is administered prior to engagement of said human patient in said motion sickness engendering activity, thereby prophylactically treating motion sickness.

14. The method of claim 13, wherein administration of said *botulinum* toxin is from one hour to up to two weeks prior to said motion sickness engendering activity.

* * * * *